US00PP25434P3

(12) United States Plant Patent
Cain

(10) Patent No.: US PP25,434 P3
(45) Date of Patent: Apr. 14, 2015

(54) GRAPEVINE 'IFG SIXTEEN'

(50) Latin Name: *Vitis vinifera*
Varietal Denomination: IFG Sixteen

(71) Applicant: David Cain, Bakersfield, CA (US)

(72) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 146 days.

(21) Appl. No.: 13/986,679

(22) Filed: May 24, 2013

(65) Prior Publication Data

US 2014/0352009 P1 Nov. 27, 2014

(51) Int. Cl.
*A01H 5/00* (2006.01)

(52) U.S. Cl.
USPC ..... Plt./205

(58) Field of Classification Search
USPC ..... Plt./205
See application file for complete search history.

*Primary Examiner* — Annette Para

(57) ABSTRACT

This invention is a new and distinct grapevine variety denominated 'IFG Sixteen'. The new grapevine is characterized by producing naturally large, ovate to slightly elongated ovate, black seedless berries which are medium firm in texture and ripen late in the growing season. Fruits normally ripen mid to late September near Delano, Calif.

1 Drawing Sheet

Latin name of the genus and species claimed: *Vitis vinifera*. Variety denomination: 'IFG Sixteen'.

BACKGROUND OF THE INVENTION

The new and distinct grapevine described and claimed herein originated from a hand pollination of the Autumn Royal variety (USDA non-patented) and bulked pollen derived from several un-named red seedless selections from the Volcani Institute hybridized in May 2001. It is unknown which selection was the actual paternal parent. The abortive seed traces were subsequently embryo cultured and the resulting plant was planted in the field in April 2002. The present variety of grapevine was selected as a single plant in September 2004 and was first asexually propagated by hardwood cuttings in December 2005 near Delano, Kern County, Calif. The resulting propagules were planted during April 2006 at the International Fruit Genetics LLC research facility near Delano, Kern County, Calif. and were found to reproduce true-to-type through at least one generation of asexual reproduction.

BRIEF SUMMARY OF THE INVENTION

The new grapevine 'IFG Sixteen' is characterized by producing naturally large, ovate to slightly elongated ovate, black seedless berries which are medium firm in texture and ripen late in the growing season. Fruits normally ripen mid to late September near Delano, Calif.

To the inventor's knowledge, the known variety which the new grapevine variety is most similar to is its parent the Autumn Royal variety. 'IFG Sixteen' can be distinguished from the Autumn Royal variety by having a broader, more desirable cluster shape and thicker and tougher peduncle and pedicle, by having a much smaller residual seed trace, by having slightly softer flesh, by having no tendency to develop an astringent flavor and by having higher, more consistent yields. 'IFG Sixteen' tolerates rain during the ripening season much better than the Autumn Royal variety. The canes of the 'IFG Sixteen' are more flexible and less brittle than the Autumn Royal variety, reducing damage during pruning and other cultural operations.

BRIEF DESCRIPTION OF THE FIGURE

The accompanying photographic illustration in FIG. 1 illustrates in full color 'IFG Sixteen'. The photograph was taken outdoors with indirect lighting. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The descriptive matter which follows pertains to 'IFG Sixteen' plants grown in the vicinity of Delano, Kern County, Calif. during 2009 and 2010, and is believed to apply to plants of the variety grown under similar conditions of soil and climate elsewhere:

Vine:

*General*.—Size — Large. Vigor — Vigorous. Density of foliage — Medium. Productivity — Very productive. Root stock — Own root. Training method — Typically spur pruned leaving 2 bud spurs.

*Trunk*.—Trunk diameter of 4-year-old vines at 30 cm above the soil line — 6.2 cm. Shape — Stocky. Straps — Short — Split. Surface texture — Shaggy. Inner bark color — Can be any of the following colors; Grey brown; N199B, and 200A, and N200A.

Shoots:

*Young shoot*.—Form of tip — Wide open. Distribution of anthocyanin coloration of tip — Absent. Intensity of anthocyanin coloration of tip — Absent. Density of prostrate hairs of tip — Medium. Density of erect hairs of tip — Absent. Color — Can be any of the following colors; Yellow green; 144A and 146A.

*Woody shoot* (*mature canes*).—Shape — Stocky. Internode length — Long; About 13.9 cm. Width at node — About 1.2 cm. Cross section — Circular. Surface — Edged. Main color — Can be any of the following colors; Grey orange; 164A, and 177A and B, and 166C and D. Density of erect hairs of nodes — None. Density of erect hairs on internodes — None. Growth of axillary shoots — Medium strong; Approximately 36.9 cm.

*Flowering shoot*.—Vigor during flowering — Strong. Attitude during flowering on shoots not tied — Semi-drooping to Drooping. Color — dorsal side of internodes — Green with Red stripes. Color — ventral side of internodes — Green. Color — dorsal side of nodes — Green with Red stripes. Color — ventral side of nodes — Green. Density of prostrate hairs of nodes — Sparse. Density of erect hairs of nodes — Very sparse. Density of prostrate hairs on internode — None. Density of erect hairs on internode — None. Anthocyanin coloration of buds — Absent.

*Tendrils*.—Distribution on the shoot (at full flowering) — Discontinuous. Length of Tendril — Long; About 32.8 cm. Thickness — Medium. Color — Green; N144A. Form — Bifurcated and trifurcated. Number of consecutive tendrils — 2 to 3.

Leaves:

*Young leaves*.—Color of upper surface of first four distal unfolded leaves — Can be any of the following colors; Yellow green; 144A and B. Average intensity of anthocyanin coloration of six distal leaves prior to flowering — Weak. Density of prostrate hairs between veins (lower surface) — Very sparse. Density of prostrate hairs on veins (lower surface) — Very sparse. Density of erect hairs between veins (lower surface) — Absent. Density of erect hairs on veins (lower surface) — Very sparse.

*Mature leaves*.—Average length — About 23.2 cm. Average width — About 22.0 cm. Mature leaf size — Large. Shape of blade — Wedge-shaped. Number of lobes — 5. Anthocyanin coloration of main veins on upper side of blade — Weak to medium. Mature leaf profile — Undulate. Blistering surface of blade upper surface — Weak to medium. Leaf blade tip — In the plane of the leaf. Undulation of margin — Slight to medium. Thickness — Medium. Undulation of blade between main and lateral veins — Overall. Shape of teeth — Mixture of both sides straight and both sides convex. Length of teeth — Medium. Ratio length/width of teeth — Equal to slightly longer than wide. Shape of upper lateral sinuses — Slightly open to lobes slightly overlapping. Depth of upper lateral sinuses — Shallow. General shape petiole sinus — Wide open to half open. Shape of base of upper leaf sinuses — U-shaped. Tooth at petiole sinus — Absent. Density of prostrate hairs between veins on lower surface of blade — Very sparse. Density if erect hairs between veins on lower surface of blade — Absent. Density of prostrate hairs on main veins on lower surface of blade — very sparse. Density of erect hairs on main veins on lower surface of blade — Sparse. Density of prostrate hairs on main veins on upper surface of blade — Sparse. Density of erect hairs on main veins on upper surface of blade — Sparse. Autumn coloration of leaves — Leaves can be a single color or combination of colors, in a mottled pattern or on the edges of the leaves; Yellow; 11A and B and C, and Purple; N77 A, and Red Purple; 59A, and Greyed purple; 187A.

*Upper surface*.—Color — Can be any of the following colors; Green; 137A and B and C. Anthocyanin coloration of main veins — Weak to medium. Surface appearance — Dull. Blistering surface of blade — Weak to medium.

*Lower surface*.—Color — Can be any of the following colors; Green; 137A and 146A. Anthocyanin coloration of main veins (lower surface) — Weak. Glossiness — Weak. Surface texture — Rugose. Surface appearance — Dull.

*Petiole*.—Length — About 15.8 cm. Length of petiole compared to middle vein — Much shorter. Density of prostrate hairs on petiole — None. Density of erect hairs on petiole — Sparse.

*Buds*.—Bud fruitfulness — Basal: Mostly fruitful. Position of first fruitful shoot on previous season cane — $1^{st}$ to $2^{nd}$ node. Time of bud burst — Medium; Mar. 14, 2012.

Flowers:

*General*.—Flower sex — Hermaphrodite. Length of first inflorescence — Medium; About 17.8 cm long by 12.8 cm wide. Position of first flowering and fruiting node — $3^{rd}$ to $4^{th}$ (current season growth). Number of inflorescence per flowering shoot — 1.1 to 2. Time of bloom — Midseason as compared with similar varieties in the growing area of Delano, Calif. Date of full bloom — May 18, 2012.

Fruit:

*General*.—Ripening period — Late season. Keeping quality — Excellent. Resistance to — Insects: Average typical of *Vitis vinifera* species. Diseases: Average typical of *Vitis vinifera* species. Refractometer test — Soluble solids: About 17.0 Brix. Brix/acid — About 56.7. Titratable acidity — About 0.3 g/100 ml. Juice pH — About 3.94.

*Cluster*.—Mature cluster length (peduncle excluded) — About 30.2 cm. Mature cluster width — About 23.4 cm. Mature cluster weight — About 2270 g. Bunch density — Medium. Number of berries — About 330. Form — Broad Conical.

*Peduncle*.—Lignification of peduncle — Strong. Length of peduncle — Medium long; Approximately 6.3 cm.

*Berry*.—Uniformity of size — Uniform. Single berry weight — About 9.5 g. Shape — Ovate to slightly elongate ovate. Seeds — Contains very small rudimentary seed traces not noticeable. Cross section — Circular. Berry dimensions — Longitudinal axis: About 3.2 cm. horizontal axis: About 2.2 cm. Berry firmness — Medium. Particular flavor — Neutral. Bloom (cuticular wax) — Weak. Berry separation from pedicel — Medium. Skin color (without bloom) — Can be any of the following colors; Greyed Purple; N186A and B.

*Skin*.—Thickness — Medium. Texture — Medium firm. Reticulation — Present. Tenacity — Tenacious to flesh.

What is claimed:

1. A new and distinct variety of grapevine as herein illustrated and described.

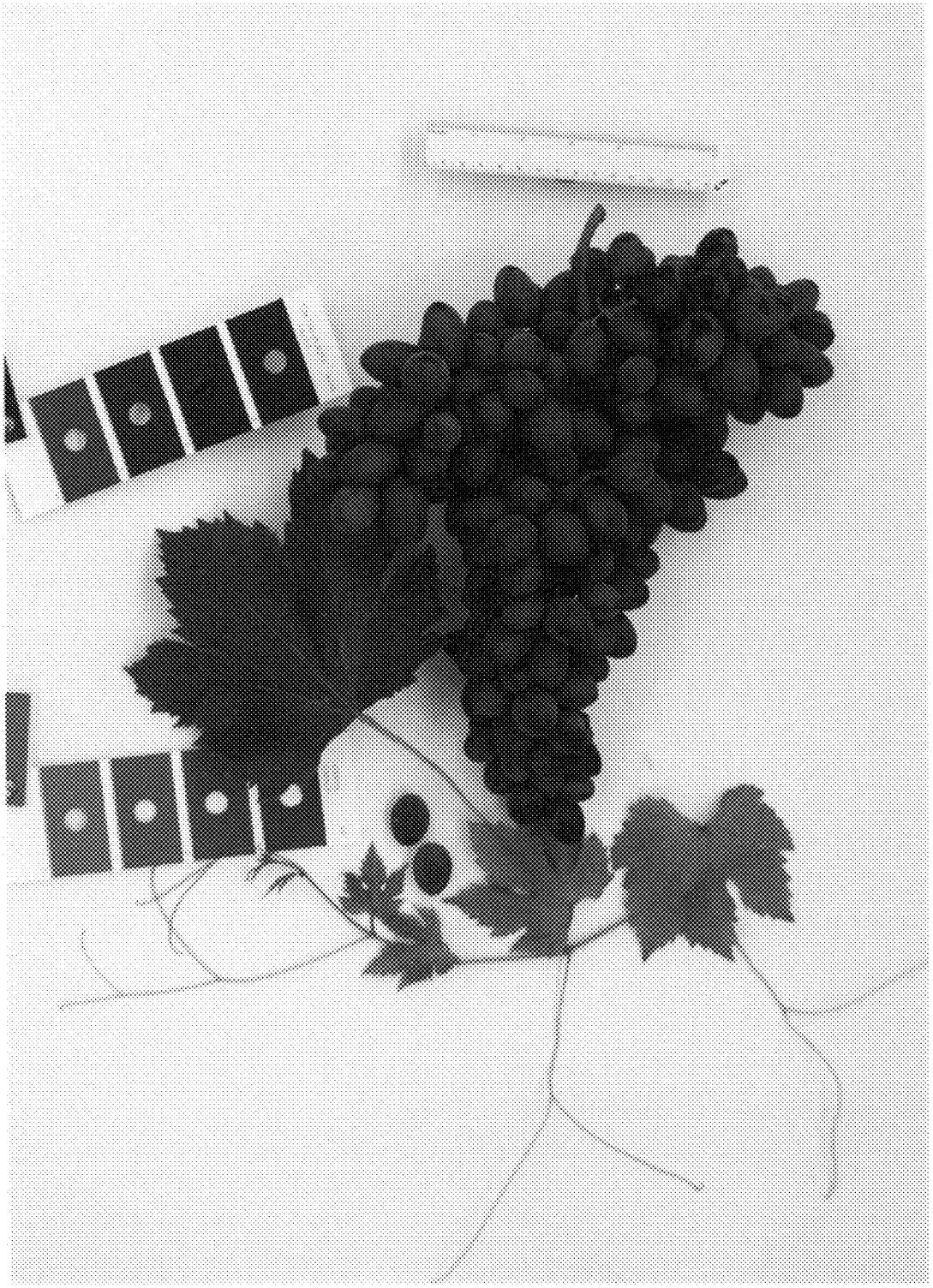

* * * * *